(12) United States Patent
Robertson

(10) Patent No.: US 7,338,948 B2
(45) Date of Patent: Mar. 4, 2008

(54) USE OF QUETIAPINE

(75) Inventor: John Robertson, Knoxville, TN (US)

(73) Assignee: AstraZeneca AB, Sodertalje (SE)

( * ) Notice: Subject to any disclaimer, the term of this patent is extended or adjusted under 35 U.S.C. 154(b) by 355 days.

(21) Appl. No.: 10/398,307

(22) PCT Filed: Aug. 31, 2001

(86) PCT No.: PCT/SE01/01879

§ 371 (c)(1),
(2), (4) Date: Apr. 3, 2003

(87) PCT Pub. No.: WO02/20019

PCT Pub. Date: Mar. 14, 2002

(65) Prior Publication Data

US 2004/0034010 A1     Feb. 19, 2004

(30) Foreign Application Priority Data

Sep. 5, 2000    (SE) .................................. 0003126

(51) Int. Cl.
*A61K 31/553*    (2006.01)
*A61K 31/554*    (2006.01)

(52) U.S. Cl. ................................................ 514/211.13
(58) Field of Classification Search ............ 514/211.13
See application file for complete search history.

(56) References Cited

U.S. PATENT DOCUMENTS 5,605,897 A    2/1997    Beasley et al.
5,627,178 A    5/1997    Chakrabarti et al.

FOREIGN PATENT DOCUMENTS

| EP | 0240228 | 11/1990 |
|---|---|---|
| EP | 0240228 B1 * | 11/1990 |
| WO | WO 97/45124 | 12/1997 |

OTHER PUBLICATIONS

Berkow, R., et al, The Merck Manual of Diagnosis and Therapy, 1992, Merck Research Laboratories, Sixteenth Edition, pp. 2102-2105, for example.*

* cited by examiner

*Primary Examiner*—San-Ming Hui
(74) *Attorney, Agent, or Firm*—Karen Cochran; Pepper Hamilton LLP

(57) ABSTRACT

A method of treating Attention Deficit Hyperactivity Disorder, Conduct Disorder and related disorders which comprises using the atypical antipychotic agent quetiapine.

22 Claims, No Drawings

USE OF QUETIAPINE

CROSS REFERENCE TO RELATED APPLICATION

This application is the U.S. National Stage filing of International Application Ser. No. PCT/SE2005/000411 filed Mar. 21, 2005, which claims priority to Swedish Application Ser. No. 0402780-1 filed Nov. 12, 2004 and Swedish Application Ser. No. 0400718-3 filed Mar. 22, 2004, each of which is incorporated herein by reference in its entirety.

This invention relates to a method of treating Attention Deficit Hyperactivity Disorder, Conduct Disorder and related disorders and in particular to the use of quetiapine in treating such disorders.

Patients with Attention Deficit Hyperactivity Disorder display symptoms including persistent inattention, hyperactivity and impulsivity. This leads to difficulties in various situations for example in the workplace, in social situations and in the academic environment. Particular manifestations include inattention, being easily distracted, not listening, making careless mistakes, failing to complete tasks and being disorganised. Patients with Hyperactivity Disorder may also display undue fidgeting, impatience, the inability to be quiet when required and excessive physical activity in inappropriate circumstances.

There are three defined sub-types of Attention Deficit Hyperactivity Disorder: 'Attention Deficit Hyperactivity Disorder, Combined Type', 'Attention Deficit Hyperactivity Disorder, Predominantly Inattentive Type' and 'Attention Deficit Hyperactivity Disorder, Predominantly Hyperactive-Impulsive Type'. These sub-types are defined in the "Diagnostic and Statistical Manual of Mental Disorders", Fourth Edition published by the American Psychiatric Association, Washington, D.C., USA. This Manual may also be referred to for greater detail on the symptoms and diagnostic features associated with Attention Deficit Hyperactivity Disorder.

Patients with Conduct Disorder display aggressive behaviour threatening or causing physical harm to others, non-aggressive behaviour causing damage to property and also theft. Again, this leads to difficulties in society, in the workplace and in the academic environment.

There are two defined sub-types of Conduct Disorder: 'Childhood-Onset Type' and 'Adolescent-Onset Type' and each may appear at a Mild, Moderate or Severe level. These sub-types and severity levels are defined in the "Diagnostic and Statistical Manual of Mental Disorders", Fourth Edition published by the American Psychiatric Association, Washington, D.C., USA. Again, this Manual may also be referred to for greater detail on the symptoms and diagnostic features associated with Conduct Disorder.

Treatment of Attention Deficit Hyperactivity Disorder, Conduct Disorder and related disorders is problematic. Psychopharmacological treatments of ADHD include psychostimulants, tricyclic medications, bupropion, clonidine and others. One third of patients with ADHD are poor responders to currently available treatments. There has been much research into the treatment of Conduct Disorder. This is a psychiatric illness highly resistant to current treatment. Upwards of 50% of adolescents with Conduct Disorder develop Antisocial Personality Disorder, usually a lifelong and disabling condition that results in exorbitant costs to society.

Quetiapine is an atypical antipsychotic agent which has good efficacy and tolerability and which is useful in the treatment of schizophrenia.

We have now unexpectedly found that quetiapine is useful in treating Attention Deficit Hyperactivity Disorder, Conduct Disorder and related disorders.

According to the present invention, we provide a method for treating Attention Deficit Hyperactivity Disorder, Conduct Disorder or a related disorder which comprises administering an effective amount of quetiapine or a pharmaceutically acceptable salt thereof to a patient in need thereof.

In another aspect, the present invention provides quetiapine or a pharmaceutically acceptable salt thereof for use in treating Attention Deficit Hyperactivity Disorder, Conduct Disorder or a related disorder.

In yet a further aspect, the present invention provides the use of quetiapine or a pharmaceutically acceptable salt thereof in the manufacture of a medicament for treating Attention Deficit Hyperactivity Disorder, Conduct Disorder or a related disorder.

In particular aspects, the present invention provides methods for treating 'Attention Deficit Hyperactivity Disorder, Combined Type', 'Attention Deficit Hyperactivity Disorder, Predominantly Inattentive Type' and 'Attention Deficit Hyperactivity Disorder, Predominantly Hyperactive-Impulsive Type'.

Quetiapine is 11-(4-[2-(2-hydroxyethoxy)ethyl]-1-piperazinyl)dibenzo[b,f][1.4]thiazepine. This compound, pharmaceutically acceptable salts thereof and its use in treating schizophrenia are described in granted European Patent No. EP 240,228 and in corresponding patents.

The method of treatment of the present invention may be conducted over a short term (5-6 weeks), medium term (1-6 months) or long term (6 months-2 years or more) treatment, and is particularly valuable in medium term and long term treatment. In a particular aspect, quetiapine does not exhibit the significant weight gain seen with some other atypical antipsychotics. Thus, it is particularly suitable for longer-term treatment.

Attention Deficit Hyperactivity Disorder and Conduct Disorder are particularly prevalent in children. Unsuccessful treatment of these disorders in children can adversely affect their entire life. Establishment of a pattern of antisocial behaviours and attitudes in their formative years can shape the future. Furthermore, inattention and related behaviour at school can lead to lower grades and again this can shape the future. Thus in a particularly important aspect, the present invention provides a method of treatment of children suffering from Attention Deficit Hyperactivity Disorder and Conduct Disorder. In one aspect the children are aged up to 7 years; in another aspect the children are in the age range 7 to 16 years.

Accordingly, the present invention particularly provides a method for treating Conduct Disorder Child-Onset Type which comprises administering an effective amount of quetiapine or a pharmaceutically acceptable salt thereof to a patient in need thereof.

Accordingly, the present invention particularly provides a method for treating Conduct Disorder Child-Adolescent Type which comprises administering an effective amount of quetiapine or a pharmaceutically acceptable salt thereof to a patient in need thereof.

In either the Child-Onset Type or the Adolescent-Onset Type, the severity may be mild, moderate or severe. Quetiapine is helpful for all conditions.

Quetiapine may be administered as the compound, 11-(4-[2-(2-hydroxyethoxy)ethyl]-1-piperazinyl)-dibenzo[b,f][1.4]thiazepine or may be administered in the form of a pharmaceutically acceptable salt. Examples of suitable salts include, for example, chloride, maleate, fumarate, citrate, phosphate, methane sulphonate and sulphate salts. Preferred salts include fumarates and a particularly preferred salt is the hemi-fumarate.

It is generally preferred that 11-(4-[2-(2-hydroxyethoxy) ethyl]-1-piperazinyl)-dibenzo[b,f][1.4]thiazepine is administered in the form of a pharmaceutically acceptable salt, and in particular a fumarate (2:1) salt.

In the treatment of the diseases and conditions mentioned above quetiapine or a pharmaceutically acceptable salt may be administered orally or parenterally in a conventional dosage form such as tablets, pills, capsules, injectables or the like. The dosage in mg/kg of body weight of the compound used to treat mammals will vary according to the size of the mammal and particularly with respect to the brain/body weight ratio. In general, a higher mg/kg dosage for a small animal such as a dog will have the same effect as a lower mg/kg dosage in an adult human. A minimum effective dosage for quetiapine or a pharmaceutically acceptable salt thereof will be about 0.5 mg/kg of body weight per day for mammals with a maximum dosage for a small mammal such as a dog, of about 200 mg/kg per day.

For humans, a dosage of about 0.5 to 40 mg/kg, for example 0.5 to 20 mg/kg per day will generally be effective. Typically, a dosage of about 50 mg to 1200 mg per day will generally be effective. Usually, a dosage of about 150 mg to 1200 mg per day will be administered, with a convenient dosage being about 500-1000 mg per day. In some groups of patients a lower dosage may be preferred such as 250 mg per day. The dosage can be given once daily or in divided doses, for example, 2 to 4 doses daily. The dose may be conventionally formulated in an oral or parenteral dosage form by compounding 25 to 500 mg per unit dosage of conventional vehicle, excipient, binder, preservative, stabiliser, flavour or the like as called for by accepted pharmaceutical practice, for example, as described in U.S. Pat. No. 3,755,340.

Quetiapine or a pharmaceutically acceptable salt may be used in pharmaceutical compositions as the sole active ingredient or may be contained in a pharmaceutical composition together with one or more other active ingredients, or it may be co-administered with one or more known drugs.

Quetiapine or a pharmaceutically acceptable salt may be administered in conjunction with one or more other agents useful for treating Attention Deficit Hyperactivity Disorder, Conduct Disorder and related disorders, for example amphetamine, methylphenidate, bupropion and tricyclic antidepressants such as desipramine, imipramine and nortriptyline.

As indicated above, where quetiapine or a pharmaceutically acceptable salt is administered in conjunction with another agent it may be administered simultaneously, sequentially or separately with that other agent or agents. Thus, as indicated above, quetiapine or a pharmaceutically acceptable salt may be formulated with the other agent or agents or may be presented as a separate formulation.

Thus, in one aspect of the present invention, there is provided a pharmaceutical composition comprising quetiapine or a pharmaceutically acceptable salt and an agent useful for treating Attention Deficit Hyperactivity Disorder, Conduct Disorder or a related disorder together with a pharmaceutically acceptable diluent or carrier.

In a further aspect there is provided a pharmaceutical composition comprising quetiapine or a pharmaceutically acceptable salt and an agent for treating Attention Deficit Hyperactivity Disorder, Conduct Disorder or a related disorder for simultaneous, sequential or separate administration.

The preparation of 11-(4-[2-(2-hydroxyethoxy)ethyl]-1-piperazinyl)-dibenzo[b,f][1.4]thiazepine and its pharmaceutically acceptable salts is described in, for example, granted European Patents Nos. EP 240,218; EP 282,236 and in International Patent Application No. PCT/GB98/02260. This compound is commercially available under the generic name quetiapine fumarate.

The invention will now be illustrated with reference to the following, non-limiting examples in which quetiapine was used as the fumarate (2:1) salt.

EXAMPLE 1

A 12-year-old Caucasian male was diagnosed with 'Conduct Disorder, Childhood Onset, Moderate Severity' and 'Attention Deficit Hyperactivity Disorder (ADHD), Combined Type' (DSM-IV diagnostic criteria). He exhibited severely disruptive behaviour including aggression towards family members. He did not meet DSM-IV criteria for other illnesses including mania.

He had been taking an amphetamine-based product (60 mg/day) and imipramine (75 mg/day) for 2 years. Prior to this treatment he took methylphenidate, although this eventually became ineffective. On presentation at this clinic, his weight was low at 74 lbs, possibly related to use of the amphetamine-based product, and his height was 56 in. Imipramine was discontinued because of associated mood instability and olanzapine was prescribed up to 15 mg/day over 6 weeks. The latter was only partially effective. The amphetamine-based product was discontinued but had to be restarted due to severely increased Attention Deficit Hyperactivity Disorder (ADHD) symptoms that prevented him from attending school. Valproate 750 mg (115 ng/mL) was prescribed for 8 weeks: no significant improvement in behaviour was noted, and his weight had increased to 93 lb. (height unchanged). Valproate was therefore discontinued. The dose of olanzapine was then tapered to 10 mg daily, although increased violence resulted in this dose being increased up to 20 mg daily. In addition, he was given lithium at gradually increasing doses up to 1125 mg/day (1.7 ng/mL). The only side effects were weight gain (an increase of 32 lb.) and mild intentional tremor. A continued lack of improvement was reported over the following 8 weeks; hence lithium was discontinued.

As a result of the minimal improvement in his condition and his ongoing rapid weight gain, the decision was made to substitute quetiapine for olanzapine and continue with the amphetamine-based product (60 mg/day). Quetiapine was initially increased from 50 to 300 mg/day; he continued to demonstrate aggression. Quetiapine was gradually increased further to 400 mg in the morning and 600 mg in the evening (ie 1000 mg/day), along with a reduction of the amphetamine-based product to 45 mg/day. He experienced a dramatic reduction of his psychiatric symptoms and no side effects. His performance at school became exceptional with 'honour roll' academic achievement. His weight stabilised at 105 lb. with a height of 60.5 in. After 90 days on quetiapine 1000 mg/day and the amphetamine-based product 45 mg/day, he and his family continue to enjoy complete resolution of previous symptoms.

EXAMPLE 2

The following illustrates representative pharmaceutical dosage forms containing the compound 11-(4-[2-(2-hydroxyethoxy)ethyl]-1-piperazinyl)-dibenzo[b,f][1,4]thiazepine fumarate (2:1).

|  | mg/tablet |
| --- | --- |
| (a) Tablet | |
| Quetiapine fumarate | 50.0 |
| Mannitol, USP | 223.75 |
| Croscarmellose sodium | 6.0 |
| Maize starch | 15.0 |
| Hydroxypropylmethylcellulose (HPMC), | 2.25 |
| Magnesium stearate | 3.0 |
| (b) Capsule | |
| Quetiapine fumarate | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

A preferred formulation is that available commercially as quetiapine fumarate.

The invention claimed is:

1. A method for treating Conduct Disorder which comprises administering an effective amount of quetiapine or a pharmaceutically acceptable salt thereof to a patient in need thereof.

2. A method according to claim 1 for treating Conduct Disorder Child-Onset Type which comprises administering an effective amount of quetiapine or a pharmaceutically acceptable salt thereof to a patient in need thereof.

3. A method according to claim 1 for treating Conduct Disorder Adolescent-Onset Type which comprises administering an effective amount of quetiapine or a pharmaceutically acceptable salt thereof to a patient in need thereof.

4. A method according to any one of claims 1 to 3 wherein quetiapine or a pharmaceutically acceptable salt thereof is administered in conjunction with one or more other agents useful for treating Conduct Disorder.

5. A method according to claim 4 wherein the one or more other agents are selected from amphetamine, methylphenidate, bupropion, desipramine, imipramine and nortriptyline.

6. A method according to claim 4 wherein quetiapine or a pharmaceutically acceptable salt thereof is administered simultaneously with one or more other agents useful for treating Conduct Disorder.

7. A method according to claim 4 wherein quetiapine or a pharmaceutically acceptable salt thereof is administered sequentially with one or more other agents useful for treating Conduct Disorder.

8. A method according to claim 4 wherein quetiapine or a pharmaceutically acceptable salt thereof is administered independent of other agents useful for treating Conduct Disorder.

9. A method according to any one of claims 1 to 3 wherein quetiapine or a pharmaceutically acceptable salt thereof is administered over a term of about 5 to about 6 weeks.

10. A method according to any one of claims 1 to 3 wherein quetiapine or a pharmaceutically acceptable salt thereof is administered over a term of about 1 month to about 6 months.

11. A method according to any one of claims 1 to 3 wherein quetiapine or a pharmaceutically acceptable salt thereof is administered over a term of about 6 months to about 2 years.

12. A method according to any one of claims 1 to 3 wherein quetiapine or a pharmaceutically acceptable salt thereof is administered for a term greater than 2 years.

13. A method according to claim 1 wherein the patient is about 7 years of age or less.

14. A method according to claim 1 wherein the patient is in the age range of about 7 years to about 16 years.

15. A method according to claim 1 wherein the quetiapine or pharmaceutically acceptable salt thereof is administered in a dose of about 0.5 mg/kg per day to about 200 mg/kg per day.

16. A method according to claim 15 wherein the quetiapine or pharmaceutically acceptable salt thereof is administered in a dose of about 0.5 mg/kg per day to about 40 mg/kg per day.

17. A method according to claim 16 wherein the quetiapine or pharmaceutically acceptable salt thereof is administered in a dose of about 0.5 mg/kg per day to about 20 mg/kg per day.

18. A method according to claim 1 wherein the quetiapine or pharmaceutically acceptable salt thereof is administered in a dose of about 50 mg to about 1200 mg per day.

19. A method according to claim 18 wherein the quetiapine or pharmaceutically acceptable salt thereof is administered in a dose of about 150 mg to about 1200 mg per day.

20. A method according to claim 19 wherein the quetiapine or pharmaceutically acceptable salt thereof is administered in a dose of about 500 mg to about 1000 mg per day.

21. A method according to claim 1 wherein the quetiapine or pharmaceutically acceptable salt thereof is administered once daily.

22. A method according to claim 1 wherein the quetiapine or pharmaceutically acceptable salt thereof is administered in divided doses.

* * * * *